United States Patent [19]
Szirth et al.

[11] Patent Number: 5,608,472
[45] Date of Patent: Mar. 4, 1997

[54] EYE IMAGING SYSTEM

[75] Inventors: Bernard C. Szirth, Methuen, Mass.; Alan L. Murphree, Los Angeles, Calif.; Steven E. Lusty, Houlka, Miss.; James A. Burris, Collierville, Tenn.

[73] Assignee: Research Development Foundation, Carson City, Nev.

[21] Appl. No.: 340,976

[22] Filed: Nov. 17, 1994

Related U.S. Application Data

[63] Continuation-in-part of Ser. No. 972,704, Nov. 6, 1992, abandoned.
[51] Int. Cl.$^6$ .................... A61B 3/14; A61B 3/10
[52] U.S. Cl. .................... 351/206; 351/219; 351/221
[58] Field of Search ................... 351/206, 212, 351/219, 221, 247

[56] References Cited

U.S. PATENT DOCUMENTS

| | | | |
|---|---|---|---|
| 3,944,341 | 3/1976 | Pomerantzeff | 351/221 |
| 4,200,362 | 4/1980 | Pomerantzeff | 351/205 |
| 4,715,703 | 12/1987 | Cornsweet et al. | 351/205 |
| 5,125,730 | 6/1992 | Taylor et al. | 351/206 |

Primary Examiner—Scott J. Sugarman
Attorney, Agent, or Firm—Fulbright & Jaworski

[57] ABSTRACT

An eye imaging system having a hand held portable image capture unit connected by cable to a housing. The hand held unit includes a light fiber optic for transmitting light to the eye, imaging and focusing optics, and a charge coupled image device. The connecting housing provides an electrical power source, light source and viewing monitor for viewing an image of the eye.

8 Claims, 7 Drawing Sheets

TUMOR OR CLOSED ANGLE IMAGING

EYE IMAGING SYSTEM

CROSS-REFERENCE TO RELATED APPLICATION

This application is a continuation-in-part of application Ser. No. 07/972,704 filed Nov. 6, 1992, entitled Eye Imaging System, now abandoned.

BACKGROUND OF THE INVENTION

The eye imaging system of the present invention is designed to capture the image of the structures in the posterior chamber of the human eye, including the retina, and any structures within the same. regions of the vitreous. Fundus cameras using 35 mm film have been used in the past for photographing the eye. However, such cameras have various limitations, are technically challenging to operate, and are limited in use. The present imager provides super wide-angle viewing of the ocular fundus, with capability for color fundus imaging, fluorescein angiography and stereoimaging. The present imager can resolve approximately 80% of the retina and capture the image with consistent digital quality. The sharp digital resolution is important to the documentation of a patient's condition for diagnosis or before and after treatment especially for a series taken over an extended period of time. The present imager provides captured digital images which may be viewed and studied immediately on a monitor screen, stored digitally for later examination and comparison, and/or printed out via a printer for hard copy documentation, or sent through telephone lines via a modem.

SUMMARY OF THE INVENTION

The present invention is directed to an eye imaging system having a housing which includes an electrical power source, a light source for providing light to the eye, and a viewing monitor for viewing an image. A hand held portable image capture unit is provided having a light fiber optic for transmitting light to the eye, imaging and focusing optics including a cornea contact lens, and a charge coupled image device. The light fiber optics includes a concentric light passageway surrounding the cornea contact lens for illuminating the eye through the cornea. A connecting cable between the housing and the image capture unit includes a control line for supplying and receiving information between the housing and the capture unit, and an electrical cable for supplying power, and a supply light fiber optic cable for supplying light from the light source to the light fiber optic in the capture unit.

Still a further object is wherein the concentric light passageway converges towards the axis of the cornea contact lens. In one embodiment the concentric light passageway includes two concentric light passages.

Still a further object of the present invention is wherein the concentric light passageway is formed by fanning out fibers from the light fiber optic and the ends of the fibers form a continuous 360° light source.

Yet a still further object is wherein the charged coupled image device is a chromatic image device and the imaging and focusing optics includes a color aberration preventing lens means.

Still a further object is wherein the aberration preventing lens means includes two sets of triplet lenses in which the triplet lens brings separated colors and blend the colors to one focal point.

A still further object of the present invention is wherein the optics include a removable cornea contact lens, condensing lens and primary lens and further includes a Goldman type lens for attachment to the portable image capture device.

Yet a further object is wherein a changeable lens is provided in the optics for providing a 15° to 150° view of the interior of the eye.

Still a further object of the present invention is wherein the light source in the housing includes a tungsten lamp.

Other and further objects, features and advantages will be apparent from the following description of the presently preferred embodiments of the invention, given for the purpose of disclosure, and taken in conjunction with the accompanying drawings.

DESCRIPTION OF THE PREFERRED EMBODIMENT

Figure 1:
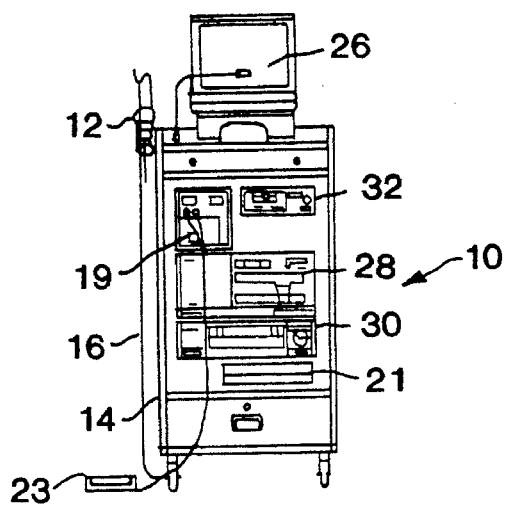
FIG. 1 is a front elevational view of the present invention.
Figure 2:
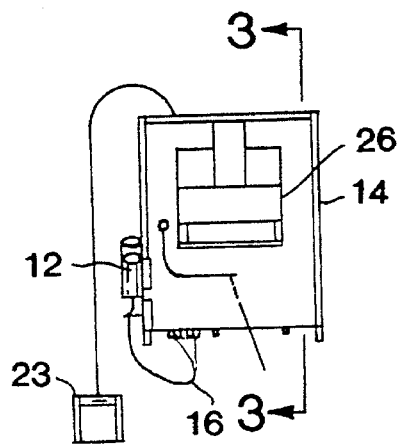
FIG. 2 is a top elevational view of the apparatus of FIG. 1.
Figure 3:
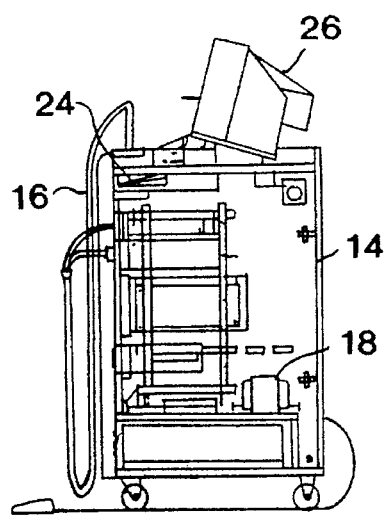
FIG. 3 is a cross-sectional view taken along the line 3–3 of FIG. 2.

Referring now to the drawings, the reference numeral 10 generally indicates the eye imaging system of the present invention and generally includes a hand held portable image capture unit 12, a suitable housing are console 14 and a connecting cable 16.

The housing 14 generally includes an electrical power source 18, a light source 20, a slide light filter 22, a keyboard 24, a viewing monitor 26, an output recorder such as a printer 28, a still video recorder such as a digital laser floppy disk 32, and/or a VHS recorder 30, a control panel 19, a charge coupled device control 21, and foot pedal control 23.

Figure 4:
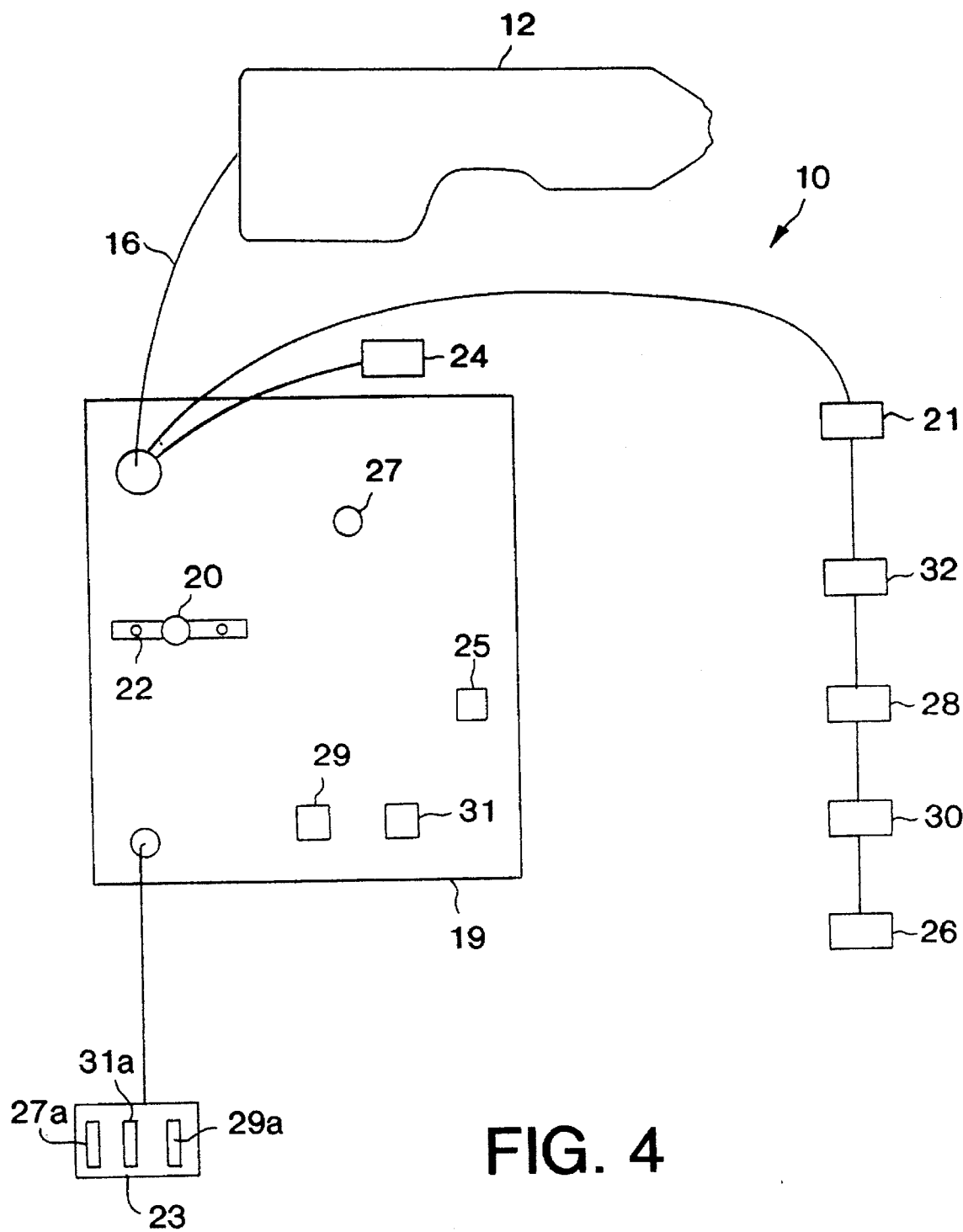
FIG. 4 is a schematic diagram of the control circuit of the apparatus of FIG. 1.

Referring now to FIG. 4 the control panel 19, in addition to including the light source 20 and slide bar filter 22, includes a power switch 25, a light intensity control 27, a focus control 29, and a capture control 31. The foot pedal control 23 includes light intensity control 27a, focus control 29a and capture control 31a thereby allowing the operator to control the operation of the apparatus 10 while holding the capture unit 12 by hands. The keyboard 24 is a white balance intensity control for insuring true color representation by the charge coupled device. The control 21 receives digital images from the capture unit 12 and converts them to an analog output for transmission to the recorder 30, the printer 28, the VHS 30, and monitor 26.

Figure 5:
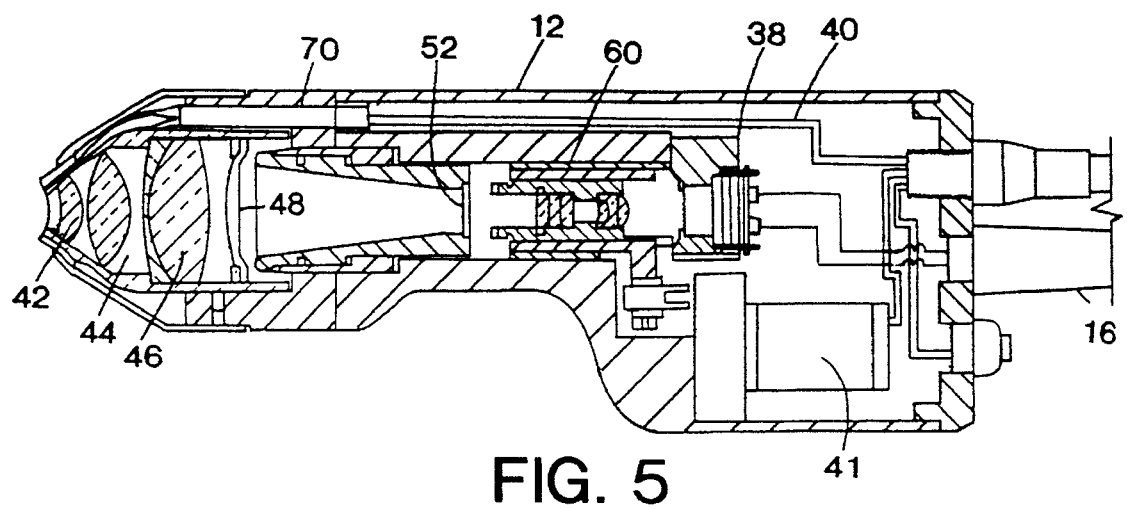
FIG. 5 is an enlarged elevational view, in cross-section, of the hand held portable image capture unit of the present invention.
Figure 6:
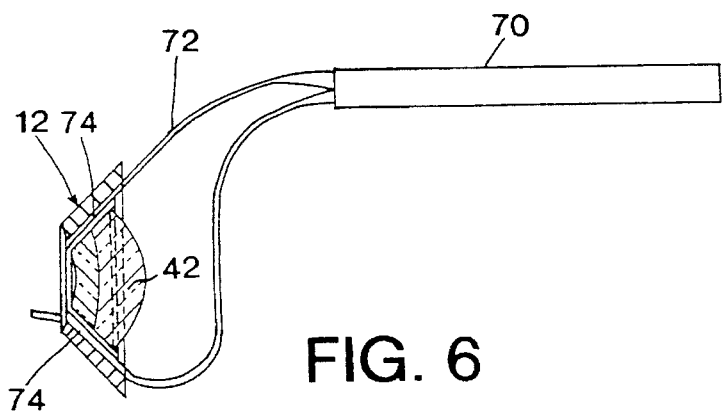
FIG. 6 is an elevational view of the light delivery assembly of FIG. passageway from a fiber sleeve.
Figure 7:
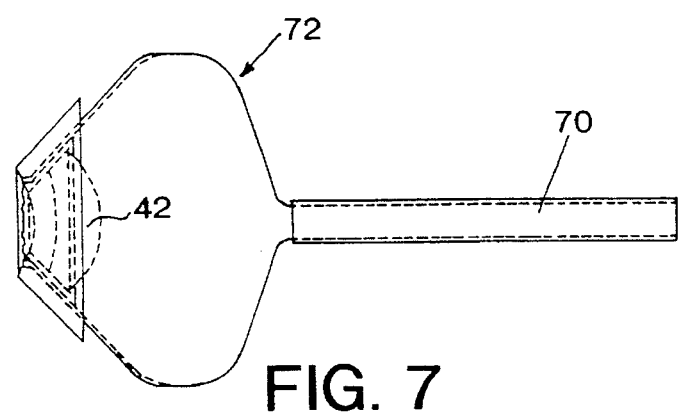
FIG. 7 is a top view of the light delivery system of FIG. 6.
Figure 12:
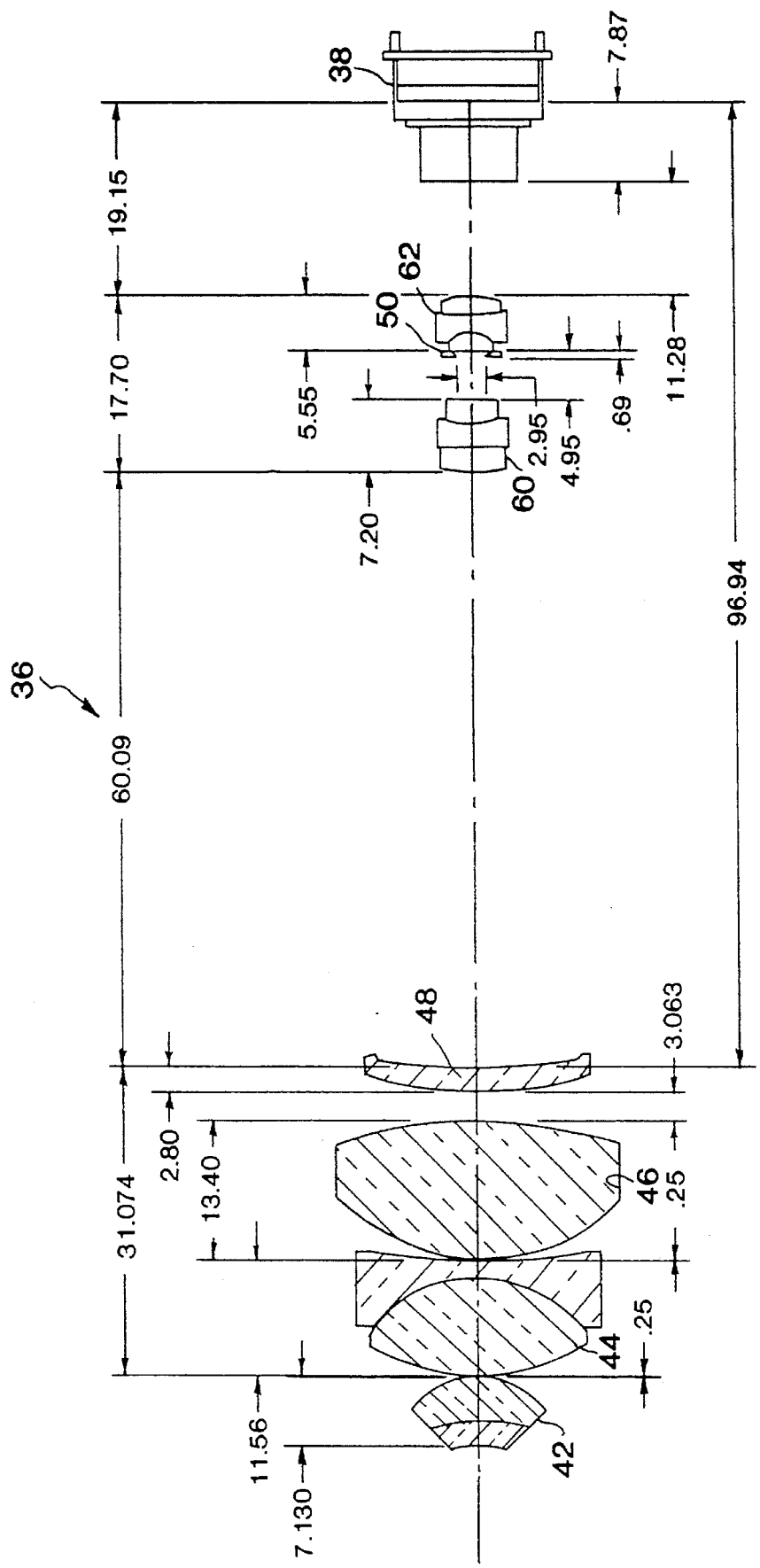
FIG. 12 is an optical layout of the various lenses in the portable capture unit of the present invention.
Figure 14:
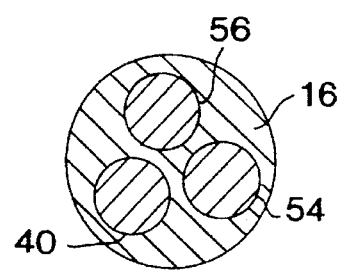
FIG. 14 is a cross-sectional view of the connecting cable between the housing and the hand held unit of the present invention.

Referring to FIG. 5 the portable image capture unit 12 is shown connected to the cable 16 which includes, as best seen in FIG. 14 a quartz fiber optic cable 40, a power cable 54 and a remote control cable 56. The portable image capture unit 12 also includes an imaging and focusing optics 36 (FIGS. 5 and 12), and a digital imaging device 38 which is a charged coupled image device such as a 0.5 charged couple device (CCD), which electronically captures the image for transmission to the CCD controller 21. The imaging and focusing optics includes, as best seen in FIGS. 5 and 12, a primary cornea contact lens 42 which is a dual lens, a primary lens 44, a condensing lens 46, a reducing lens 48, collectively known as the primary lens system, an iris diaphragm 50 and an insertable lens 52 (FIG. 5). The primary lens system is releasably connected to the unit 12 by set screws (not shown) and may be removed as will be more fully discussed hereinafter. The iris diaphragm 50 may be set at a suitable F/Stop setting to control the depth of field for optimal visualization and imaging of the features of interest. The insertable lens 52 effectively controls the field of view imaged on the CCD 38 and can be changed to provide a varied view of the posterior chamber of the human eye varying from a 15° view to a 150° span. Focus motor 41 actuates the focus of the optics 36.

Preferably the CCD 38 is a chromatic image device for obtaining color images of the posterior chamber which provides a true color representation of the posterior chamber and any pathology present and by using different wave lengths of light views different layers of the posterior chamber. In addition, color imaging enables the unit 10 to provide stereo imaging and makes it easier to determine if a pathology is active or calcified. However, in obtaining color images by the CCD 38 a lens system must be added to the imaging and focusing optics 36 to prevent color aberration. That is, the colors of red, green and blue will normally separate and will create a hazy image if the color aberration is not corrected. Thus, a first triplet lens 60 is provided in the imaging and focusing optics (FIGS. 5 and 12) which brings the separated colors to one common focal point and a second set of triplet lenses 62 puts the focal point on the focal plane of the CCD 38. Thus, each of the triplets 60 and 62 include three lenses for acting on the different wave lengths of the colors of red, green and blue thereby preventing any color aberrations and maintaining true color representation. However, if desired the chromatic CCD 38 may also be used for monochromatic imaging.

In order to obtain true representation of the posterior chamber of the eye and any pathologies, and in particular to obtain true color, it is important to have uniform light temperature and uniform light distribution. Referring now to FIGS. 5–9, a concentric light passageway is provided surrounding the cornea contact lens 42 for illuminating the eye through the cornea. That is, a continuous 360° light source is provided which gives an even distribution of light to the posterior chamber of the eye and also has the advantage of requiring a lower light intensity. The quartz fiber optic cable 40 is connected to a bundle 70 of sleeve fiber optic fibers in which the individual fibers 72 are fanned outwardly and the ends 74 are positioned to form a continuous 360° light source around the cornea lens 42 in which the ends 74 provide a concentric light passageway surrounding the cornea contact lens 42 for providing a light source directed through the cornea.

Figure 8:
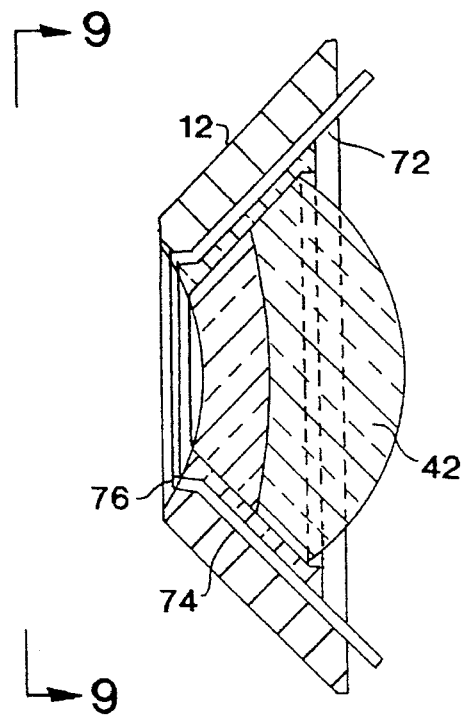
FIG. 8 is an enlarged elevational view, in cross-section, of the ends of the fanned out fiber optics about the cornea contact lens.
Figure 9:
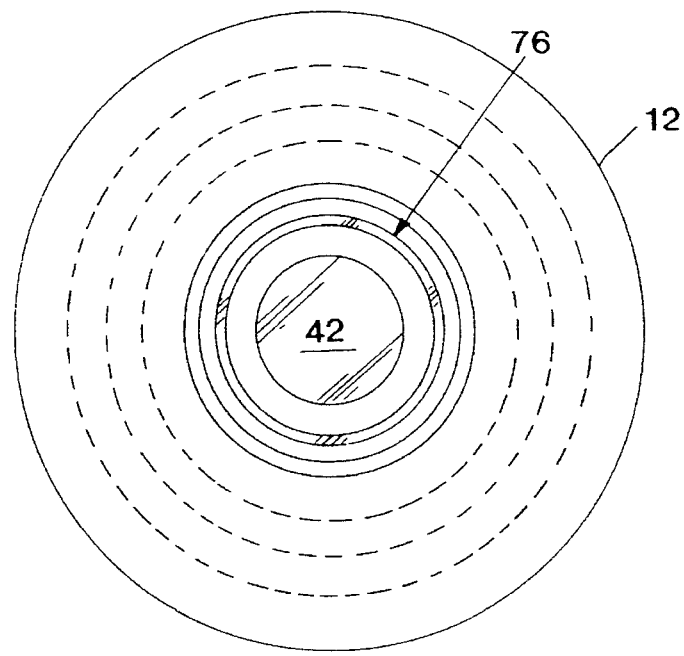
FIG. 9 is a cross-sectional view taken along the line 9—9 of FIG. 8.

In one embodiment, as best seen in FIGS. 8 and 9, the outer ends 76 of the fanned out fiber optic fibers 72 converge towards the axis of the cornea contact lens 42 for giving a larger field of view. For example only, the ID of the concentric light passage formed by the ends 76 may be 7.5 mm and have a thickness of 0.016 mm and converges at an angle of 10° relative to the access of the lens 42, and include approximately 2,000 fibers. However, various other angles of incident may be provided to the cornea for compensating for various cornea shapes. However, the concentric light passageway provides a lower incident of reflection from the cornea, and light is distributed at a low intensity and at a uniform spread out distribution.

Figure 10:
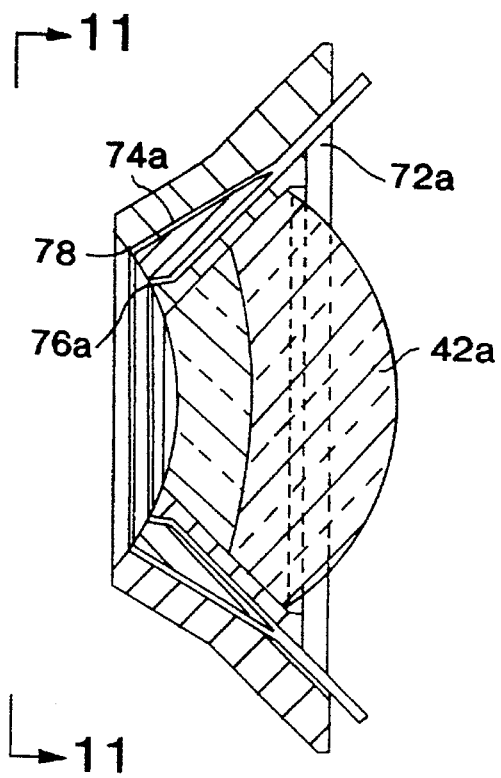
FIG. 10 is an enlarged elevational view, in cross-section, illustrating another embodiment providing dual concentric light passageways about the cornea contact lens.
Figure 11:
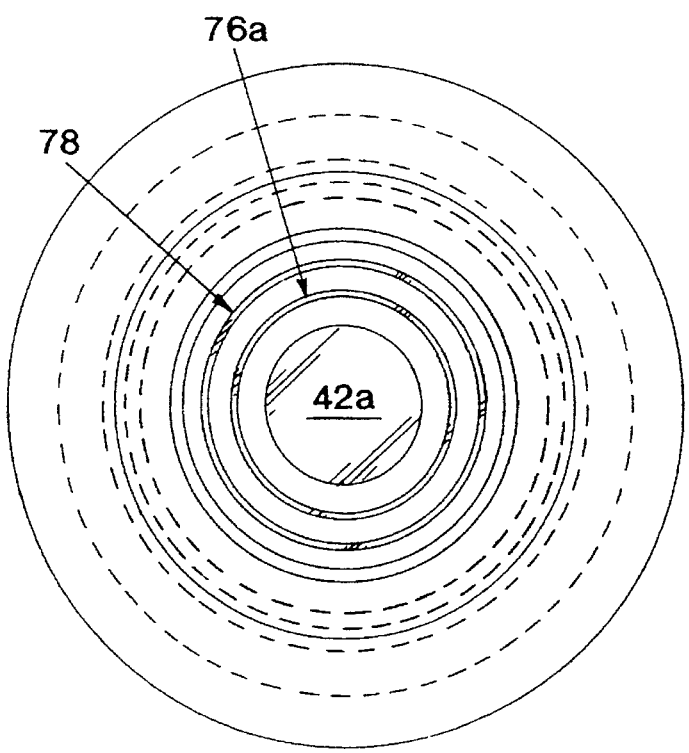
FIG. 11 is a view taken along the line 11—11 of FIG. 10.

Referring now to FIGS. 10 and 11, a further embodiment is provided in which the concentric light passageway includes two concentric light passages wherein like parts to that shown in FIGS. 8 and 9 are similarly numbered with the addition of the suffix However, in addition to the concentric passageway formed by the ends 76a, a second concentric passageway is formed by ends 78 of the fanned out fibers 72a which further increases the distribution of light to the posterior chamber. In this embodiment the ends 78 of the second concentric passageway converges towards the axis of the cornea contact lens at a different angle from the ends 76a and for example only, may converge at an angle of 30°. Another advantage of the multiple concentric like passageways is the ability to allow the unit 10 to accommodate abnormal cornea shapes such as the difference between pediatric and geriatric patients.

Figure 13:
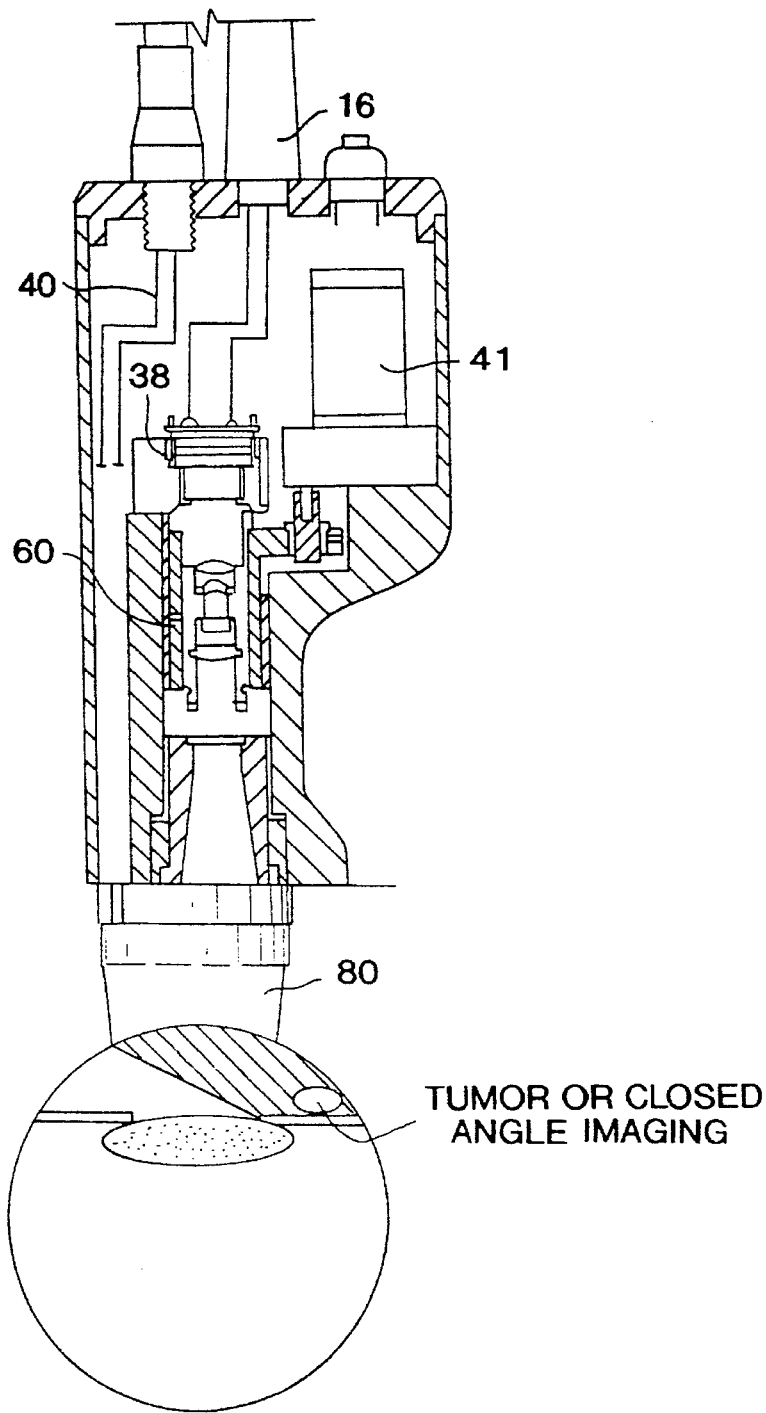
FIG. 13 is an elevational view, in cross-section, illustrating the removal of the objective head of the capture unit along with the lens system and the substitution of a Goldman type lens thereon.

Referring now to FIG. 13, the portable capture unit 12 is shown with the primary lens system removed and a Goldman type lens 80 has been attached thereto which contains its own mirror which allows close angle imaging in the interior chamber such as for tumor detection. Or if desired, the primary lens system may be removed and the hand held portable capture unit 12 may be used for external imaging of the eye. Further, if desired a fiber optic cable port (not shown) may be provided for communication with the cable 40 for providing transclera illumination to the exterior of the eye which provides indirect illumination. This is useful in the adult eye that has cataracts or dilates poorly.

Excess light may cause damage (light toxicity) to the eye. However, the CCD 38 is advantageous over conventional 35 mm cameras as it requires less light and therefore less illumination of the interior of the eye. Furthermore, the use of the concentric light passage sources of FIGS. 5–9 provide lower light point intensity as the light is distributed in low intensity and spread out. Furthermore, the light source 20 is preferably a tungsten lamp which provides a continuous soft light as compared to incandescent lights or a flash or strobe.

The side light filter 22 may be slid in place over the lamp 20 and filtered light is sent out over the connecting cable 16 and the fiber optic cable 40. Various types of filters may be used such as yellow T, orange, red, fluorescein, or green. By use of the filters, the operator may select the spectral composition of the illumination for either black and white or color imaging, red free viewing and imaging of the fundus, or deep blue stimulation of Fluorescein for imaging and angiography.

In the housing 14, the output image signal from the capture unit 12 is transmitted over the connecting cable 16 and digitally displayed in the monitor 26 thereby allowing the operator to insure that the best view is obtained. At the operator's command, the digital signal may be copied to long term digital storage on the computer floppy diskette 32 for later reference and/or computer manipulation or may be printed out on a color digital printer 28 for hard copy file documentation.

Finally, by proper manual translation and multiple image capture, the imager 10 can provide stored image for stereo imaging of structures of clinical interest in the eye.

The present invention 10 is particularly advantageous as the hand held portable capture unit is particularly useful for bedridden patients or babies in incubators. Furthermore, the output from the CCD 38 is immediately shown on the monitor 26 and therefore good images can be preserved without trial and error. In addition, the digital output may be recorded, printed out, compared side-by-side, reworked, and less storage is required.

The present eye imaging system can record retinal images in either color or monochromatic mode using a 15° to 150° degree of view, and a portable hand held system allows super wide angle retinal documentation extending to 150°. The present invention can store images in a time and space saving fashion while allowing telephone transfer of full color images via a modem anywhere in the world in a few seconds. The present low white light system requires no flash to record an image. This is a great advantage especially when concerned with photophobic patients or the fear of phytotoxicity. Finally, this invention affords the recording of continuous VHS tape of any view that is captured by the capture unit be it color, monochromatic or fluorescein angiography. This greatly enhances teaching capabilities to both the medical and patient population.

While any suitable components may be used in the unit 10, for purposes of disclosure, the viewing monitor 26 may be Model CT-1382-VY sold by Panasonic. The output recorder 28 may be Model UP5200MD sold by Sony. The VCR 30 may be Model AG-2520SQPB sold by Panasonic. The floppy recorder 32 may be Model AG810 sold by Panasonic. The CCD 38 may be Model LX-450A sold by Optronics.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts, may be made without departing from the spirit of the invention and the scope of the appended claims.

What is claimed is:

1. An eye imaging system comprising, a console having an electrical power source, a light source for providing light to the eye, and a viewing monitor for viewing a captured image, a hand held portable image capture unit having a light passageway for transmitting light to an eye from the light source, imaging and focusing optics including a corneal contact lens, a color aberration preventing means, an iris diaphragm, and a chromatic charged coupled image device for receiving light from the eye through the imaging and focusing optics, said light passageway coupled to a concentric light passage adjacent the corneal contact lens for illuminating the eye through a cornea, and a connecting cable between the console and the image capture unit having a control line for supplying and receiving information between the console and the capture unit, and an electric cable for supplying power.

2. The system of claim 1 wherein the concentric light passage converges toward the axis of said corneal contact lens.

3. The system of claim 1 wherein the concentric light passage includes two concentric light passages, first and second light passages, wherein said second concentric light passage is concentric with said first light passage.

4. The system of claim 1, wherein the concentric light passage is formed by fanning out fiber optic fibers from the light source and ends of the fibers form a continuous 360° light source.

5. The system of claim 1 wherein the aberration preventing lens means includes two sets of triplet lenses, and said two sets of triplet lenses receive separate colors and blend said colors to one focal point.

6. The system of claim 1 wherein the imaging and focusing optics include a removable corneal contact lens, a condensing lens and a primary lens, and further include a Goldman type lens for attachment to the portable image capture unit.

7. The system of claim 1 including a changeable lens in the imaging and focusing optics for providing a 15° to 150° view of an interior of the eye.

8. The system of claim 1 wherein the light source in the console includes a tungsten lamp.

* * * * *

UNITED STATES PATENT AND TRADEMARK OFFICE
CERTIFICATE OF CORRECTION

PATENT NO. : 5,608,472  
DATED : March 4, 1997  
INVENTOR(S) : Bernard C. Szirth et al.

Page 1 of 1

It is certified that error appears in the above-identified patent and that said Letters Patent is hereby corrected as shown below:

Column 2,  
Line 32, after "FIG." add -- 6 illustrating the fanning out of fiber optic fibers into a concentric light --

Column 4,  
Line 29, after "suffix" add -- "a" --  
Line 34, change "converges" to -- converge --

Signed and Sealed this

Twenty-eighth Day of May, 2002

Attest:

Attesting Officer

JAMES E. ROGAN  
*Director of the United States Patent and Trademark Office*